United States Patent [19]

Yu et al.

[11] 4,105,782

[45] * Aug. 8, 1978

[54] TREATMENT OF ACNE AND DANDRUFF

[76] Inventors: Ruey J. Yu, 4400 Dexter St., Philadelphia, Pa. 19128; Eugene J. Van Scott, 1138 Sewell La., Rydal, Pa. 19046

[ * ] Notice: The portion of the term of this patent subsequent to May 3, 1994, has been disclaimed.

[21] Appl. No.: 720,787

[22] Filed: Sep. 7, 1976

Related U.S. Application Data

[60] Continuation-in-part of Ser. No. 556,423, Mar. 7, 1975, Pat. No. 3,988,470, and Ser. No. 556,424, Mar. 7, 1975, Pat. No. 3,984,566, each is a division of Ser. No. 445,231, Feb. 25, 1974, Pat. No. 3,920,835, which is a continuation-in-part of Ser. No. 394,269, Sep. 4, 1973, Pat. No. 3,879,537.

[51] Int. Cl.$^2$ .............................................. A61K 31/35
[52] U.S. Cl. .................................... 424/283; 424/279; 424/285; 424/316; 424/317; 424/320; 424/DIG. 4
[58] Field of Search ............... 424/180, 283, 316, 317, 424/311, 320, DIG. 4

[56] References Cited

U.S. PATENT DOCUMENTS

| | | | |
|---|---|---|---|
| 2,118,566 | 5/1938 | De Wayne Miles | 424/317 |
| 2,717,850 | 9/1955 | Schmitz | 424/319 |
| 3,068,145 | 12/1962 | Glenn | 424/320 |
| 3,096,244 | 7/1963 | Ehrhart et al. | 424/320 |
| 3,124,506 | 3/1964 | Holman | 424/317 |
| 3,549,544 | 12/1970 | Johnson | 252/152 |
| 3,639,623 | 2/1972 | Ritschel et al. | 424/329 |
| 3,640,883 | 2/1972 | Gotte et al. | 424/320 |
| 3,666,863 | 5/1972 | Swanbeck | 424/317 |
| 3,806,593 | 4/1974 | Swanbeck et al. | 424/311 |
| 3,879,537 | 4/1975 | Van Scott et al. | 424/311 |

*Primary Examiner*—Leonard Schenkman
*Attorney, Agent, or Firm*—Leblanc & Shur

[57] ABSTRACT

Preventive as well as therapeutic treatment to alleviate the symptoms of diseases characterized by defects in keratinization consisting of the topical application of a solution, lotion, cream or shampoo containing one or more of the α-hydroxy or α-keto acid amides and/or ammonium salts is disclosed. The compounds include amide and/or ammonium salt forms of citric acid, glycolic acid, glucuronic acid, galacturonic acid, glucuronolactone, gluconolactone, α-hydroxybutyric acid, α-hydroxyisobutyric acid, malic acid, mandelic acid, pyruvic acid, β-phenyllactic acid, β-phenylpyruvic acid, saccharic acid, tartaric acid, tartronic acid and β-hydroxybutyric acid. The therapeutic composition may include one or more of the compounds present in a total amount of from 1 to 20 percent. Topical application to affected areas has been found to achieve from a substantial to a complete remission of dandruff and acne.

9 Claims, No Drawings

TREATMENT OF ACNE AND DANDRUFF

This application is related to our copending patent application Ser. No. 598,224, filed July 23, 1975, now U.S. Pat. No. 4,021,572, hereby incorporated by reference, and is a continuation-in-part of our copending applications Ser. Nos. 556,423 and 556,424, filed Mar. 7, 1975, now U.S. Pat. Nos. 3,988,470 and 3,984,566, respectively, hereby incorporated by reference, which applications are divisions of application Ser. No. 445,231, filed Feb. 25, 1974, now U.S. Pat. No. 3,920,835, which in turn was a continuation-in-part of application Ser. No. 394,269, filed Sept. 4, 1973, now U.S. Pat. No. 3,879,537.

This invention relates to a treatment for diseases characterized by defective keratinization including dandruff and acne and specifically to compounds which have been found to be effective when topically applied to heal the skin lesions associated with these diseases in humans.

Disease conditions characterized by defects in keratinization are relatively common and many different treatments have been prescribed in the past with varying degrees of effectiveness. In each of these disease conditions the process whereby the epidermal cells mature and form a surface layer (stratum corneum) is defective. Therefore, the signs and symptoms of diseases associated with defective keratinization are due to an overproduction of cells and/or their retention in the stratum corneum for abnormally prolonged periods.

In our previous application Ser. No. 445,231, filed Feb. 25, 1974, now U.S. Pat. No. 3,920,835, and entitled TREATMENT OF DISTURBED KERATINIZATION, a treatment was described for dandruff, acne and palmar and plantar hyperkeratosis.

As described in our aforementioned application, certain lower alipathic compounds having 2 to about 6 carbon atoms and preferably having α-carbon functionality were found to be effective against dandruff, acne and palmar and plantar hyperkeratosis. These compounds include glycolic acid, citric acid, malic acid, tartronic acid, tartaric acid, glucuronic acid, pyruvic acid, methyl pyruvate, ethyl pyruvate, α-hydroxyisobutyric acid and α-hydroxybutyric acid.

In our continued studies of topical treatment for dandruff and acne, we found that the aforementioned α-hydroxy and α-keto acids in concentrations of more than 5 percent in a solution or cream could inflame or irritate skin involved with the above skin conditions. When these acids are neutralized with metal alkalis such as sodium hydroxide or potassium hydroxide the sodium or potassium salts of α-hydroxy or α-keto acid thus formed do not penetrate human skin readily, and although the salts formed are non-irritating they are also ineffective.

We have now discovered that dandruff and acne may be successfully prevented or treated with amide and/or ammonium salts of α or β-hydroxyacids or α-keto acids. Generally, the amide may be formed from acid anhydride or lactone and ammonia or any organic amine of primary or secondary family. The ammonium salt may be formed directly from acid and an organic amine of primary, secondary or tertiary amine.

Preferred organic primary amines may include any alkylamines such as methylamine and ethylamine; ethanolamines such as monoethanolamine and monoisopropanolamine; and diamines such as ethylenediamine and 1,2-diaminopropane.

Preferred organic secondary amines may include dialkylamines such as dimethylamine and diethylamine; diethanolamine and diisopropanolamine; N-methylethanolamine and N-ethylethanolamine.

Preferred organic tertiary amines may include trialkylamines such as trimethylamine and triethylamine; triethanolamine; N-methyldiethanolamine and triisopropanolamine.

It has been established through tests on humans having dandruff or acne that topical application of a solution, lotion, cream or shampoo containing from 1 to 20 percent of at least one amide and/or the ammonium salt of the present invention, and preferably from 2 to 10 percent thereof, is therapeutically effective, when applied on a daily basis, to cause, within about 2 to 4 weeks time, a return of the affected areas to a normal skin condition. If two or more amides and/or ammonium salts are used in a composition of this invention, the total concentration of the compounds is preferred not to exceed 10 percent by volume of the composition. It has also been found in humans having extremely oily skin or having frequent occurrence of dandruff or acne lesions that topical application of the aforementioned composition of the present invention is effective, when applied on a daily basis, in preventing development of dandruff or acne lesions.

Accordingly, it is the object of this invention to provide a cosmetic composition containing at least one of the amides and/or the ammonium salts, which when topically applied will reliably prevent the development of dandruff or acne.

It is another object of this invention to provide a medicinal composition containing at least one of the amides and/or the ammonium salts, which when topically applied will substantially alleviate the symptoms of dandruff or acne.

It is still another object to provide a method for treating dandruff or acne with a nonirritant and nontoxic solution, lotion, cream or shampoo of the present invention.

It is still another object to provide a safe and efficient method for treating the symptoms of dandruff or acne through regular topical application of a medicinal composition which will promote healing within about two or four weeks.

It is still another object of this invention to provide a method for formulating a cosmetic as well as medicinal composition in solution, lotion, cream or shampoo which when topically applied at least daily to skin prone to lesions of dandruff or acne will prevent the development of dandruff, or acne, or result in a restoration of normal healthy skin condition.

PREPARATION OF THE THERAPEUTIC COMPOSITIONS

When α-hydroxy or α-keto acids were prepared in a composition containing 5 to 20 percent by weight of the compounds in an aqueous solution the pH of the solution was about 2 or less. In treatment of dandruff and acne we found that the above composition with low pH could cause some skin irritation (redness and sensation of burning) of some of the patients. It was therefore desirable to develop compositions which were therapeutically effective but not irritant.

Most inorganic alkalis, forming inorganic salts with α-hydroxy acids or α-keto acids that do not readily penetrate human skin, cannot be used to neutralize the acidity of solutions of these acids. But, it has been discovered that certain organic bases and ammonium hydroxide may be successfully used to raise the pH of the solution containing α-hydroxy or α-keto acids without comprising the therapeutic efficaciousness of the active ingredients. Under such conditions the active ingredients are in the form of amide or ammonium salts. Preferred organic bases include organic primary, secondary or tertiary amines.

The organic primary amines may include alkylamines such as methylamine and ethylamine; ethanolamine such as monoethanolamine and monoisopropanolamine; diamines such as ethylenediamine and 1,2-diaminopropane. The organic secondary amines include dialkylamines such as dimethylamine and diethylamine; diethanolamine and diisopropanolamine; N-methylethanolamine and N-ethylethanolamine. The organic tertiary amines include trialkylamines such as trimethylamine and triethylamine; triethanolamine; N-methyldiethanolamine and triisopropanolamine.

The α and β-hydroxy acids and α-keto acids of the present invention include citric acid, glycolic acid, glucuronic acid, galacturonic acid, glucuronolactone, gluconolactone, α-hydroxybutyric acid, α-hydroxyisobutyric acid, malic acid, mandelic acid, pyruvic acid, β-phenyllactic acid, β-phenylpyruvic acid, saccharic acid, tartaric acid, tartronic acid and β-hydroxybutyric acid.

Generally, a nonirritating composition of this invention should have a pH of the solution, lotion, cream or shampoo between 3.5 and 7.5.

To prepare an amide or an ammonium salt of the present invention the lactone or α-hydroxy acid or α-keto acid is allowed to react at room temperature with an ammonium hydroxide or an organic amine in aqueous or alcoholic aqueous solution. Generally, the amide or ammonium salt thus formed needs no isolation procedure and may be directly incorporated into the therapeutic composition.

The initial concentration of α-hydroxy acid or β-keto acid may range from 1 to 20 percent by volume of the total composition. The preferred concentration range, however, is from 2 to 10 percent.

Ordinarily distilled water is preferred as a solvent in the preparation of the composition. To improve the suitability of the composition for topical use on human skin, ethanol and propylene glycol may be added to the aqueous solution. The ratio of each vehicle may vary; however, the preferred concentration of ethanol and propylene glycol should not exceed 70 percent and 40 percent, respectively.

In a variety of methods for formulating a composition of the present invention two or more than two different amides or ammonium salts may also be utilized in the composition.

The prophylactic as well as therapeutic composition may also be prepared in a form of lotion, cream or shampoo. In these instances, well-known, cosmetically or pharmaceutically acceptable ingredients are incorporated into the vehicles to prepare lotions, creams or shampoos according to this invention.

The following are illustrative examples of formulations of compositions according to this invention. Although the examples utilize only selected formulations useful according to this invention, it should be understood that the following examples are illustrative and not limited. Therefore, any of the aforementioned acids and amines may be substituted according to the teachings of this invention in the following formulations.

EXAMPLE 1

Glycolic acid, 10 grams was dissolved in 10 ml of water and the solution admixed with 50 ml of ethanol and 10 ml of propylene glycol. Ethanolamine, also known as 2-aminoethanol, 1 ml was added to the solution. Sufficient water was then added to make 100 ml of composition. This composition had a pH of 3.5.

EXAMPLE 2

A glycolic acid 20 percent solution partially neutralized was prepared as follows: Glycolic acid, 20 grams was dissolved in 20 ml of water and the solution admixed with 50 ml of ethanol. Ethanolamine, 13 ml, was added to the solution. Sufficient water was then added to make 100 ml of composition. This composition had a pH of 5.

EXAMPLE 3

Glycolic acid, 10 grams was dissolved in 10 ml of water and the solution admixed with 50 ml of ethanol and 10 ml of propylene glycol. Diethanolamine, 10 ml, was added to the solution. Sufficient water was then added to make 100 ml of composition. This composition had a pH of 4.7.

EXAMPLE 4

Glycolic acid, 10 grams, was dissolved in 10 ml of water and the solution admixed with 50 ml of ethanol and 10 ml of propylene glycol. N-Methyldiethanolamine, 10 ml, was added to the solution. Sufficient water was then added to make 100 ml of composition. This composition had a pH of 4.5.

EXAMPLE 5

Glycolic acid, 10 grams was dissolved in 10 ml of water and the solution admixed with 50 ml of ethanol and 10 ml of propylene glycol. Triethanolamine, 10 ml, was added to the solution. Sufficient water was then added to make 100 ml of composition. This composition had a pH of 4.1.

EXAMPLE 6

A composition of two active ingredients was prepared as follows: Glycolic acid, 5 grams, and citric acid, 5 grams, were dissolved in 20 ml of water and the solution admixed with 50 ml of ethanol and 10 ml of propylene glycol. N-Ethyldiethanolamine, 10 ml, was added to the solution. Sufficient water was then added to make 100 ml of composition. This composition had a pH of 4.5.

EXAMPLE 7

A composition of two active ingredients was prepared as follows: Glycolic acid, 10 grams, and citric acid, 5 grams, were dissolved in 20 ml of water and the solution admixed with 50 ml of ethanol and 10 ml of propylene glycol. Ethanolamine, 8 ml, was added to the solution. Sufficient water was then added to make 100 ml of composition. This composition had a pH of 5.7.

EXAMPLE 8

A composition of an α-hydroxy acid partially neutralized with ammonium hydroxide was prepared as follows: Glycolic acid, 10 ml, was dissolved in 10 ml of water and the solution admixed with 50 ml of ethanol and 10 ml of propylene glycol. Concentrated ammonium hydroxide solution (NH$_3$29%), 7 ml, was added to the solution. Sufficient water was then added to make 10 ml of composition. This composition had a pH of 5.2.

EXAMPLE 9

| Part A: | Polyoxyethylene sorbitan monooleate (hereinafter Tween 80) | 5 grams |
| --- | --- | --- |
|  | Cetyl alcohol | 20 grams |
|  | Cholesterol | 0.4 gram |
|  | Squalene | 0.2 gram |
| Part B: | Water | 45 ml |
|  | Propylene glycol | 10 ml |
|  | Glycolic acid | 10 grams |
|  | Ethanolamine | 7 ml |
|  | Mannitol | 2 grams |

Heat Part A to 75° C and heat Part B to 77° C. Add Part B slowly to Part A with agitation. Continue agitation until the mixture is congealed. The water-washable cream thus prepared has a pH of 4.7.

EXAMPLE 10

| Part A: | Tween 80 | 5 grams |
| --- | --- | --- |
|  | Cetyl alcohol | 15 grams |
|  | Stearyl alcohol | 5 grams |
|  | Cholesterol | 0.4 gram |
|  | Squalene | 0.2 gram |
| Part B: | Water | 59 ml |
|  | Propylene glycol | 10 ml |
|  | Glycolic acid | 4 grams |
|  | Triethanolamine | 2 ml |

Heat Part A to 75° C and heat Part B to 77° C. Add Part B slowly to Part A with agitation. Continue agitation until the mixture is congealed. The water-washable cream thus prepared has a pH of 3.5.

EXAMPLE 11

Glycolic acid, 5 grams, was dissolved in 40 ml of water and ethanolamine, 5 ml, was added slowly with stirring. Triethanolamine lauryl sulfate 50 ml was added to the mixture. This composition had 5 percent active ingredient in a shampoo formulation, pH 7.4.

EXAMPLE 12

Glycolic acid, 14 grams, was dissolved in 16 ml of water and triethanolamine, 20 ml, was added slowly with stirring. Triethanolamine lauryl sulfate 50 ml was added to the mixture. This shampoo formulation had 14 percent active ingredient, pH 4.3.

TEST RESULTS

Dandruff

Twelve patients with severe dandruff problems were instructed to rub into the scalp the shampoo preparation of Example 11 twice weekly. After each shampoo the patients were advised to apply topically the after-shampoo solution of Example 1 onto the scalp. This two-step topical treatment prevented all signs of dandruff, i.e., formation of scales on the scalp in all 12 patients. Relief was observed within about 1 to 2 weeks in each case and normal skin condition was observed to be maintained at least 1 to 2 weeks after treatment was terminated. On continual use it was also discovered that twice weekly topical application of the above preparations could prevent the development of dandruff.

Acne

Fifty patients having comedonous or moderate to severe papular-pustular acne were instructed to apply topically the solution preparation of Example 1 twice daily on the affected areas of the skin for 4 weeks. Forty-one of 50 patients showed substantial reduction in the number of acne lesion after 4 to 6 weeks of topical treatment.

A second group of 24 patients having comedonous or moderate to severe papular-pustular acne were instructed to apply topically first the solution preparation of Example 1, then the cream preparation of Example 9 twice daily on the affected areas of the skin for 4 weeks. Twenty-two of 24 patients showed substantial reduction in the number of acne lesions after 4 to 6 weeks of topical treatment. On continued use it was also found that twice daily topical application of the cream preparation of Example 9 prevented the development of new acne lesions.

The invention may be embodied in other specific forms without departing from the spirit or essential characteristics thereof. The present embodiment, therefore, is to be considered in all respects as illustrative and not restrictive, the scope of the invention being indicated by the appended claims rather than by the foregoing description, and all changes which come within the meaning and range of equivalency of the claims are, therefore, intended to be embraced therein.

What is claimed and desired to be secured by United States Letters Patent is:

1. A method for alleviating the symptoms of acne or dandruff in humans: topically applying to involved areas of the body an effective amount of a composition comprising: a therapeutically effective amount of a product prepared by reacting, in aqueous or alcoholic aqueous solution at least one member selected from the group consisting of citric acid, glycolic acid, glucuronic acid, galacturonic acid, glucuronolactone, gluconolactone, α-hydroxy-butyric acid, α-hydroxyisobutyric acid, malic acid, pyruvic acid, β-phenyllactic acid, β-phenylpyruvic acid, saccharic acid, mandelic acid, tartaric acid, tartronic acid and β-hydroxybutyric acid and a base selected from the group consisting of ammonium hydroxide, an organic primary, secondary, or tertiary alkylamine, alkanol amine, diamine, dialkylamine, dialkanolamine, alkylalkanol amine, trialkylamine, trialkanol amine, dialkyl alkanol amine, or alkyl dialkanolamine wherein the alkyl or alkanol substituent has from 1 to 8 carbon atoms in a pharmaceutically acceptable vehicle.

2. The method of claim 1 wherein the reaction product is present in a concentration of from 1 up to about 20 percent by volume of the total composition.

3. The method of claim 1 wherein the reaction product is present in a concentration of from 2 up to about 10 percent by volume of the total composition.

4. The method of claim 1 wherein the reaction product comprises a product prepared from a member selected from the group consisting of citric acid, glycolic acid, glucuronic acid, galacturonic acid, glucuronolactone, gluconolactone, mandelic acid, α-hydroxybutyric acid, α-hydroxyisobutyric acid, malic acid, pyruvic acid, β-phenyllactic acid, β-phenylpyruvic acid, saccharic acid, tartaric acid, tartronic acid and β-hydroxybutyric acid and a member selected from the group consisting of ammonium hydroxide, methylamine, ethylamine, monoethanolamine, monoisopropanolamine, ethylenediamine, 1,2-diaminopropane, dimethylamine, diethylamine, diethanolamine, diisopropanolamine, N-methylethanolamine, N-ethylethanolamine, triethylamine, triethanolamine, N-methyl-diethanolamine, and triisopropylamine.

5. The method of claim 1 wherein the vehicle is at least one member selected from the group consisting of water, ethanol, and propylene glycol present therein in a concentration of up to 99, 70, and 40 percent, respectively.

6. The method of claim 1 wherein the pH thereof is from about 3.5 to about 7.5.

7. The method of claim 1 wherein the vehicle is a shampoo.

8. The method of claim 1 wherein the vehicle is a water-washable cream.

9. The method of claim 1 wherein the vehicle is a lotion.

* * * * *